(12) United States Patent
Doerksen et al.

(10) Patent No.: US 7,590,517 B2
(45) Date of Patent: Sep. 15, 2009

(54) METHODS, SYSTEMS, AND COMPUTER PROGRAM PRODUCTS FOR COMPUTATIONAL ANALYSIS AND DESIGN OF AMPHIPHILIC POLYMERS

(75) Inventors: Robert Doerksen, Philadelphia, PA (US); Bin Chen, Baton Rouge, LA (US); William F. DeGrado, Media, PA (US); Michael L. Klein, Ocean City, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 71 days.

(21) Appl. No.: 10/446,171

(22) Filed: May 28, 2003

(65) Prior Publication Data
US 2004/0107056 A1 Jun. 3, 2004

Related U.S. Application Data

(60) Provisional application No. 60/383,884, filed on May 28, 2002.

(51) Int. Cl.
G06G 7/48 (2006.01)
(52) U.S. Cl. ........................................................ 703/11
(58) Field of Classification Search .................... 703/11
See application file for complete search history.

(56) References Cited

U.S. PATENT DOCUMENTS

2004/0102941 A1 5/2004 Lopez et al.
2004/0215400 A1 10/2004 Slovic et al.

FOREIGN PATENT DOCUMENTS

WO WO 02/072007 A2 9/2002
WO WO 02/100295 A2 12/2002

OTHER PUBLICATIONS

Ballone et al. "Polycarbonate Simulations with a Density Functional Based Force Field," J. Phys. Chem (1999) vol. 103, pp. 5387-5398.*
Brooks, B.R. et al., "CHARMM: A Program for Macromolecular Energy, Minimization, and Dynamics Calculations," *Journal of Computational Chemistry*, John Wiley & Sons, Inc., vol. 4, No. 2, 1983, pp. 187-217.
Car, R. and Parrinello, M., "Unified Approach for Molecular Dynamics and Density-Functional Theory," *Physical Review Letters*, The American Physical Society, vol. 55, No. 22, Nov. 25, 1985, pp. 2471-2474.
Chen, B. et al., "Thermodynamic Properties of the Williams, OPLS-AA, and MMFF94 All-Atom Force Fields for Normal Alkanes," *Journal of Physical Chemistry B*, American Chemical Society, vol. 102, No. 8, Mar. 17, 1998 (Published on Web), pp. 2578-2586.
Chen, B. and Siepmann, J. I., "Transferable Potentials for Phase Equilibria. 3. Explicit-Hydrogen Description of Normal Alkanes," *Journal of Physical Chemistry B*, American Chemical Society, vol. 103, No. 22, Jun. 6, 1999 (Published on Web), pp. 5370-5379.
Chen, B. et al., "Monte Carlo Calculations for Alcohols and Their Mixtures with Alkanes, Transferable Potentials for Phase Equilibria. 5. United-Atom Description of Primary, Secondary, and Tertiary Alcohols," *Journal of Physical Chemistry*, American Chemical Society, vol. 105, No. 15, Mar. 24, 2001 (Published on Web), pp. 3093-3104.
Chipot, C. and Pohorille, A., "Structure and dynamics of small peptides at aqueous interfaces A multi-nanosecond molecular dynamics study," *Journal of Molecular Structure (Teochem)*, Elsevier Science B.V., 1997, pp. 529-535.
Chipot, C. et al., "Early Events in the Folding of an Amphipathic Peptide: A Multinanosecond Molecular Dynamics Study," *Proteins: Structure, Function, and Genetics*, Wiley-Liss, Inc., vol. 36, No. 4, Sep. 1, 1999, pp. 383-399.

(Continued)

*Primary Examiner*—Jerry Lin
(74) *Attorney, Agent, or Firm*—Sterne, Kessler, Goldstein & Fox P.L.L.C.

(57) ABSTRACT

Methods, systems, and computer program products for computational polymer processing including, without limitation, computational amphiphilic polymer design, conformational energy minimization, generation and refinement of torsional parameters for sub-units of potential polymers, generation of modified force field parameters, and prediction of conformational information for potential polymers. A target polymer backbone or portion thereof is identified. Small model compounds that have structural connectivities that are similar to structural connectivities of the target polymer backbone or portion thereof, are identified, whereby the combination of the small model compounds serve as a model of the target polymer or portion thereof. Gradient-corrected density functional theory ("DFT") torsional potentials are calculated for the small model compounds, wherein energies are calculated at unconstrained and constrained geometries of the selected small model compounds. New torsional parameters are then obtained from the DFT torsional potentials. The new torsional parameters are combined with other terms to form a modified (or new) force field for the target polymer backbone or portion thereof. Molecular dynamics and configurational-biased Monte Carlo ("MD/MC") simulations are performed using the modified force field, whereby results of the MD/MC simulations serve as predicted conformation properties of the target polymer backbone. The predicted conformation properties for the multiple target polymer backbones are then used to select one or more of the target polymer backbones as candidate amphiphilic polymer backbones for synthesis.

11 Claims, 3 Drawing Sheets

OTHER PUBLICATIONS

Martin, M.G. and Siepmann, J.I., "Transferable Potentials for Phase Equilibria. 1. United-Atom Description of *n*-Alkanes," *Journal of Physical Chemistry B*, American Chemical Society, vol. 102, No. 8, Feb. 19, 1998, pp. 2569-2577.

Martin, M.G. and Siepmann, J.I., "Novel Configurational-Bias Monte Carlo Method for Branched Molecules. Transferable Potential for Phase Equilibria. 2. United-Atom Description of Branched Alkanes," *Journal of Physical Chemistry B*, American Chemisty Society, vol. 103, No. 15, Apr. 15, 1999, pp. 4508-4517.

Moore, P. B. et al., "Simulation of the HIV-1 Vpu transmembrane domain as a pentameric bundle," *FEBS Letters*, Federation of European Biochemical Societies, vol. 431, No. 2, Jul. 17, 1998, pp. 143-148.

Panagiotopoulos, A.Z., "Direct determination of phase coexistence properties of fluids by Monte Carlo simulation in a new ensemble," *Molecular Physics*, Taylor & Francis Ltd., vol. 61, No. 4, 1987, pp. 813-826.

Panagiotopoulos, A.Z. et al., "Phase equilibria by simulation in the Gibbs ensemble—Alternative derivation, generalization and application to mixture and membrane equilibria," *Molecular Physics*, Taylor & Francis Ltd, vol. 63, No. 4, 1988, pp. 527-545.

Pohorille, A. et al., "Interactions of anesthetics with the membrane-water interface," *Chemical Physics*, Elsevier Science B.V., vol. 204, 1996, pp. 337-345.

Röthlisberger, U. et al., "The torsional potential of perfluoro *n*-alkanes: A density functional study," *The Journal of Chemical Physics*, American Institute of Physics, vol. 104, No. 7, Feb. 15, 1996, pp. 3692-3700.

Siepmann, J.I. and Frenkel, D., "Configurational bias Monte Carlo: a new sampling scheme for flexible chains," *Molecular Physics*, Taylor & Francis Ltd., vol. 75, No. 1, 1992, pp. 59-70.

Smit, B. et al., "Computer simulations in the Gibbs ensemble," *Molecular Physics*, Taylor & Francis Ltd., vol. 68, No. 4, 1989, pp. 931-950.

Tew, G.N. et al., "De novo design of biomimetic antimicrobial polymers," *Proceedings of the National Academy of Sciences*, vol. 99, No. 8, Apr. 16, 2002, pp. 5110-5114.

Vlugt, T.J.H. et al., "Improving the efficiency of the configurational-bias Monte Carlo algorithm," *Molecular Physics*, Taylor & Francis Ltd., vol. 94, No. 4, 1998, pp. 727-733.

Zhong, Q. et al., "Two possible conducting states of the influenza A virus M2 ion channel," *FEBS Letters*, Federation of European Biochemical Societies, vol. 473, No. 2, May 12, 2000, pp. 195-198.

Zhong, Q. et al., "Molecular Dynamics Simulation of a Synthetic Ion Channel," *Biophysical Journal*, Biophysical Society, vol. 74, Jan. 1998, pp. 3-10.

Zhong, Q. et al., "The M2 channel of influenza A virus: a molecular dynamics study," *FEBS Letters*, Federation of European Biochemical Societies, vol. 434, No. 3, Sep. 4, 1998, pp. 265-271.

Leach, A.R., *Molecular Modeling: Principles and Applications*, Second Edition, Pearson Education, 2001, ISBN 0-582-38210-6, pp. 8, 303 and 478.

Leach, A.R., *Molecular Modeling: Principles and Applications*, Second Edition, Pearson Education, 2001, ISBN 0-582-38210-6, pp. 8, 303 and 478.

International Search Report from PCT Application No. PCT/US03/16879, filed May 28, 2003, 6 pages, mailed Nov. 6, 2003.

* cited by examiner

METHODS, SYSTEMS, AND COMPUTER PROGRAM PRODUCTS FOR COMPUTATIONAL ANALYSIS AND DESIGN OF AMPHIPHILIC POLYMERS

CROSS-REFERENCE TO RELATED APPLICATIONS

This application claims priority to U.S. Provisional Application Ser. No. 60/383,884, titled, Force Field Program, filed on May 28, 2002, incorporated herein by reference in its entirety.

STATEMENT REGARDING FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates generally to computational molecular design and, more particularly, to identification of stable conformations of polymer fragments and development of torsional parts of force fields for polymer backbones.

2. Related Art

Conventional computational molecular design approaches do not provide, among other features, adequate torsional parameters for mixtures of peptides and non-peptide units. What is needed are methods, systems, and computer program products for computational polymer processing including, without limitation, computational amphiphilic polymer design, conformational energy minimization, generation and refinement of torsional parameters for sub-units of potential polymers, generation of modified force field parameters, and prediction of conformational information for potential polymers.

SUMMARY OF THE INVENTION

The present invention is directed to methods, systems, and computer program products for computational polymer processing including, without limitation, computational amphiphilic polymer design, conformational energy minimization, generation and refinement of torsional parameters for sub-units of potential polymers, generation of modified force field parameters, and prediction of conformational information for potential polymers.

In accordance with the invention, a target polymer backbone or portion thereof is identified. Small model compounds that have structural connectivities that are similar to structural connectivities of the target polymer backbone, or portion thereof, are identified, whereby the combination of the small model compounds serve as a model of the target polymer or portion thereof.

Gradient-corrected density functional theory ("DFT") torsional potentials are calculated for the small model compounds. This preferably includes selecting small model compounds that have torsional patterns that are similar to torsional patterns of the target polymer backbone. This preferably includes calculating energies at unconstrained and constrained geometries of the selected small model compounds. More particularly, this preferably includes calculating the energies at the unconstrained and constrained geometries using a parallelized plane-wave Car-Parrinello CPMD computer program. Preferably, the geometries are pre-optimized with simulated annealing.

New torsional parameters are then obtained from the DFT torsional potentials. After full geometry optimization is performed on each of the small model compounds, using DFT, the new torsional parameters are obtained using an iterative process described herein.

The new torsional parameters are combined with other terms to form a modified (or new) force field for the target polymer backbone or portion thereof. Molecular dynamics and configurational-biased Monte Carlo ("MD/MC") simulations are performed using the modified force field, whereby results of the MD/MC simulations serve as predicted conformation properties of the target polymer backbone. The steps above provide predicted conformation properties of the target polymer backbone. The predicted conformation properties are compared against laboratory results for the small model compounds.

The steps above are preferably repeated for one or more additional target polymer backbones or portions thereof, and the predicted conformation properties for the multiple target polymer backbones are used to select one or more of the multiple target polymer backbones as candidate polymer backbones for synthesis. Alternatively, the predicted conformation properties for the multiple target polymer backbones are used to select one or more of the multiple target polymer backbones as candidate amphiphilic polymer backbones for synthesis.

The DFT optimized geometries for the target polymer or portion thereof are preferably used to determine one or more of the following:

structure of oligomers, monomeric units, or portions of a target molecules;

relative stabilities of particular conformations; and/or partial atomic charges and multipole moments that potentially have a bearing on the functioning of the target polymer.

Fitted torsional energies that are developed in accordance with the invention are combined with bond stretching, bending, one-four, van der Waals, and electrostatic potentials obtained from CHARMM and TraPPE force fields, whereby the results serve as the modified force field for the target polymer.

Additional features and advantages of the invention will be set forth in the description that follows. Yet further features and advantages will be apparent to a person skilled in the art based on the description set forth herein or may be learned by practice of the invention. The advantages of the invention will be realized and attained by the structure particularly pointed out in the written description and claims hereof as well as the appended drawings.

It is to be understood that both the foregoing summary and the following detailed description are exemplary and explanatory and are intended to provide further explanation of the invention as claimed.

BRIEF DESCRIPTION OF THE DRAWINGS/FIGURES

The present invention will be described with reference to the accompanying drawings, wherein like reference numbers indicate identical or functionally similar elements. Also, the leftmost digit(s) of the reference numbers identify the drawings in which the associated elements are first introduced.

DETAILED DESCRIPTION OF THE INVENTION

I. Introduction

Figure 1:
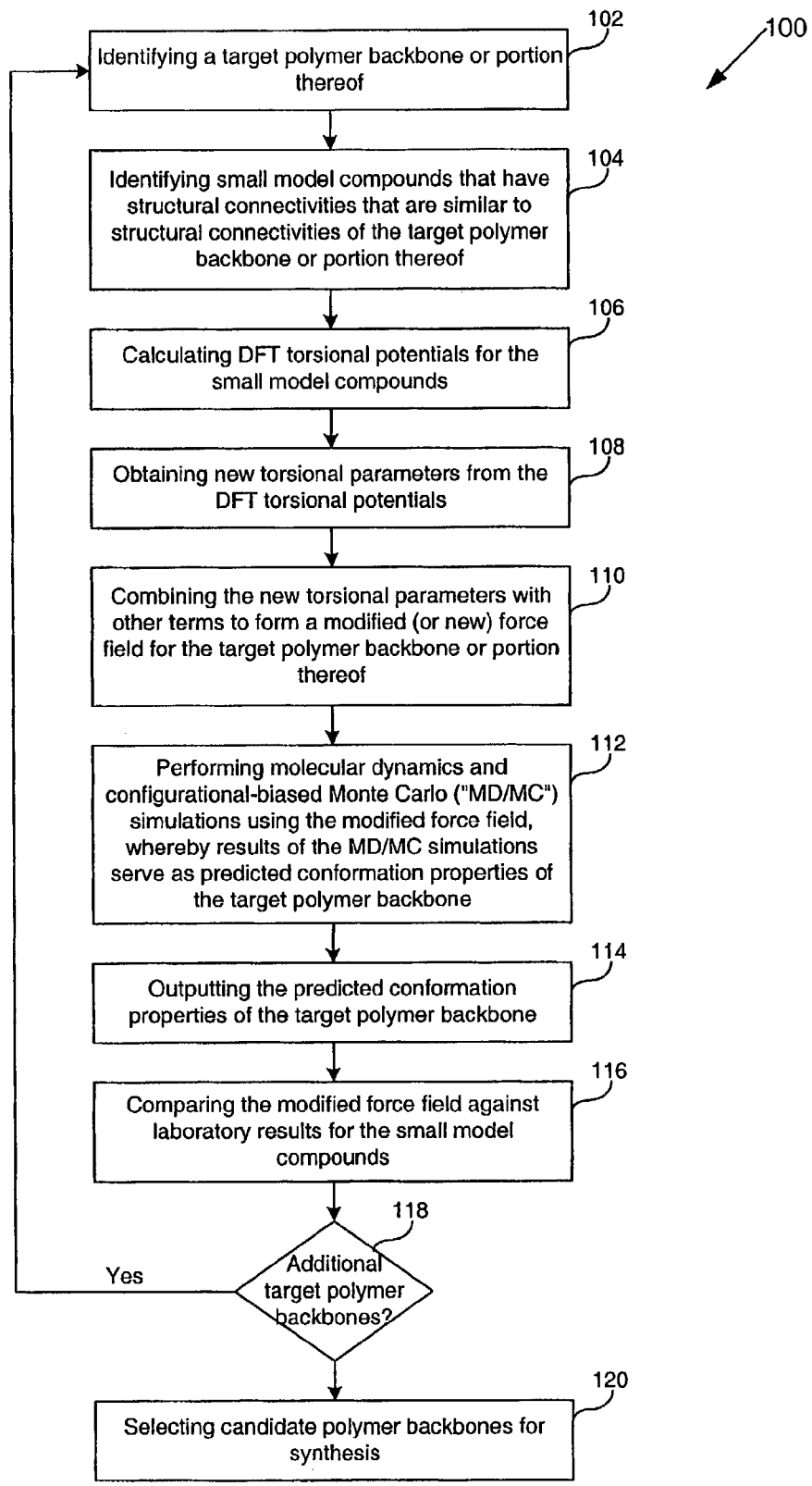
FIG. 1 is a process flowchart that illustrates an example method for predicting conformation properties of polymer backbones, in accordance with the present invention.

The present invention is directed to methods, systems, and computer program products for computational polymer processing including, without limitation, computational amphiphilic polymer design, conformational energy minimization, generation and refinement of torsional parameters for sub-units of potential polymers, generation of modified force field parameters, and prediction of conformational information for potential polymers.

The present invention is further directed to computational methods for designing polymers that adopt well-defined secondary structures. The present invention is useful for, among other things, designing and analyzing a variety of antimicrobial polymers that are simpler in structure and hence less expensive to produce than either alpha- or beta-peptides. In accordance with the present invention, amphiphilic polymers are designed based on aryl and alkyl amide, ester, aryl hydrazide, aryl oxalamide, and urea backbones.

The present invention is further directed to computational methods for predicting low-energy repeating conformations for a variety of polymers. Based on the low-energy conformations, polar and hydrophobic substituents are computationally added to provide amphiphilic structures.

In accordance with the present invention, new torsional parameters are generated for sub-units of one or more target oligomers. The new torsional parameters are included in a modified force field for the one or more target oligomers. The new torsional parameters are preferably generated from torsional potentials that are calculated with density functional theory calculations ("DFT"). The new torsional parameters are also preferably calculated using higher level calculations than those implemented in conventional methods.

II. Computational Analysis and Design

The present invention is directed to, among other features, gradient-corrected density functional theory ("DFT") calculations and other ab initio methods to search for stable conformations of selected polymer fragments and to develop the torsional parts of the force field for the polymer backbones. Molecular dynamics ("MD") simulations are performed on crystal structures of model compounds to check the accuracy of the force fields by comparing to X-ray data. Configurational-biased Monte Carlo ("MC") and MD simulations determine how polymer conformation is related to backbone and side-chain architecture, how polymer conformation is influenced by solvent, and also to predict hydrophobicity and/or hydrophobic moments. Large-scale MD simulations are used to study the dynamic binding process of amphiphilic polymers at the lipid/water interface, in order to explore details of antibacterial mechanisms. For discussions of MC, see:

Siepmann, J. K., and Frenkel, D., "Configurational-bias Monte Carlo: A New Sampling Scheme for Flexible Chains," Mol. Phys., 75, 59-70 (1992);

Martin, M. G., and Siepmann, J. I., "Novel Configurational-bias Monte Carlo Method for Branched Molecules. Transferable Potentials for Phase Equilibria. 2. United-atom Description of Branched Alkanes," J. Phys. Chem., B 103, 4508-4517 (1999); and Vlugt, T. J. H., et al., "Improving the Efficiency of the Configurational-bias Monte Carlo Algorithm," Mol. Phys., 94, 727-733 (1998); all of which are incorporated herein by reference in their entireties.

To economize the overall design process, an important element is the screening process aided by the multi-level computational approaches. The large set of polymer backbones built above are screened for various properties using cost-effective computer experiments before they are synthesized and tested in laboratory experiments. The conformations of the polymers are governed mainly by their torsional and intra-molecular hydrogen-bonding potentials. Therefore, an important part of the theoretical effort is to prepare modified force fields, which will be able to treat accurately any polymer or oligomer that fits the desired design motif.

Ab initio MD methods are an alternative approach for studying dynamic conformational properties, but they are generally only computationally affordable for relatively small polymer molecules and much shorter time scales than can be readily handled by classical MD. In accordance with the present invention, it is now possible to use standard force fields for all interactions excepts torsions, provided that the parameters are optimized based on molecules that are similar to those used in the MD calculation.

In accordance with the invention, DFT torsional potentials are developed for small model compounds that share the basic structural connectivity of the polymer backbone. The DFT torsional potentials are applied to modify the force fields for MD/MC simulations to predict conformations of the polymer backbones. The predicted conformational properties are used to select candidates for synthesis. Development of backbone torsional potentials are described below.

During development of backbone torsional potentials, fitted torsions are generated. The fitted torsions are combined with bond stretching, bending, one-four, van der Waals, and electrostatic potentials borrowed from the CHARMM (see, Brooks, B. R., et al., "CHARMM: A Program for Macromolecular Energy Minimization and Dynamics Calculations," J. Comp. Chem., 4, 187-217 (1983), incorporated herein by reference in its entirety), and/or TraPPE force fields (see: Martin, note 103, cited above; and Chen, B., et al., "Monte Carlo Calculations for Alcohols and Their Mixtures With Alkanes. Transferable Potentials for Phase Equilibria. 5. United-Atom Description of Primary, Secondary, and Tertiary Alcohols., J. Phys. Chem., B 105, 3093-3104 (2001), incorporated herein by reference in their entireties).

Initial structures can be obtained with the Gaussian package (see, Frisch, M., et al., "Gaussian 98," (Revision A.7), Gaussian, Inc., Pittsburgh, Pa., 1998, incorporated herein by reference in its entirety). A parallelized, plane-wave Car-Parrinello CPMD computer program (see: Car, R, and Parrinello, M., "Unified Approach for Molecular Dynamics and Density Functional Theory," Phys. Rev. Lett., 55, 2471-2474 (1985); Röthlisberger, U., et al, "The Torsional Potential of Perfluoro n-alkanes: A Density Functiaonl Study," J., Chem. Phys., 104, 3692-3700 (1996); and Hutter, J.; Alavi, A.; Deutsch, T.; Bemasconi, M.; Goedecker, St.; Marx, D.; Tuckerman, M.; Parrinello, M. CPMD version 3.4. MPI für Festkörperforschung and IBM Research Laboratory, Stuttgart and Zürich, 1995-2000; all of which are incorporated herein by reference in their entireties), is used to obtain energies at the minimum and constrained geometries. Apart from their role in developing force field torsional parameters, the DFT calculations are also used to determine: the structure of oligomers, monomeric units, or portions of the target molecules; the relative stabilities of particular conformations; and other properties, such as partial atomic charges and mulipole moments, that may have a bearing on the functioning of the target polymers.

Before applying a mixed force field to investigate conformations using MD simulations, it is useful to verify that the force field is able to yield satisfactory predictions of the structure and thermodynamic properties for those molecules that have similar torsional patterns and for which experimental data are available. Data obtained from crystal structures is preferably used for the verification process because the experimental conformation of an individual molecule is available. Such a test is relatively comprehensive because the crystal conformation is determined by both intra- and inter-molecular interactions.

Ab initio CPMD calculations are preferably used for crystal structure studies to further optimize force fields. Gibbs ensemble and configurational-bias MC algorithms are preferably used to evaluate the force field since phase equilibrium properties are sensitive to the choice of the interactions.

For discussions of Gibbs ensemble, see:

Panagiotopoulos, A. Z., "Direct Determination of Phase Coexistence Properties of Fluids by Monte Carlo Simulation in a New Ensemble," Mol. Phys., 61, 813-236 (1987);

Panagiotopoulos, A. Z., et al., "Phase Equilibria by Simulation in the Gibbs Ensemble. Alternative Derivation, Generalization, and Application to Mixture and Membrane Equilibria," Mol. Phys., 63, 527-545 (1988); and Smit, B., et al., "Computer Simulations in the Gibbs Ensemble," Mol. Phys., 68, 931-950 (1989); all of which are incorporated herein by reference in their entireties.

For a discussion of configurational-bias algorithms, see: Siepmann, J. K.; Martin, M. G.; and Vlugt, T. J. H., which is cited and incorporated by reference above.

For discussion of interactions, see:

Martin, M. G., and Siepmann, J. I., "Transferable Potentials for Phase Equilibria. 1. United Atom Description of n-alkanes," J. Phys. Chem., B 102, 2569-2577 (1998);

Chen, B., and Siepmann, J. I., "Transferable Potentials for Phase Equilibria. 3. Explicit-HydrogenDescription of n-alkanes," J. Phys. Chem., B 103, 5370-5379 (1999); and Chen, B., Martin, M. G., and Siepmann, J. I., "Thermodynamic Properties of the Williams, OPLS-AA and MMFF94 All-Atom Force Fields for Normal Alkanes," J. Phys. Chem. B 102, 2575-2586 (1998); all of which are incorporated herein by reference in their entireties.

After verification of the force field, conformational properties of potential polymer candidates are evaluated. For example, candidates are selected depending on whether they can adopt folding patterns similar to those of antimicrobial peptides. In other words, candidates are selected depending on whether they can adopt a periodic structure with polar groups and apolar groups lined up on the opposite sides. The conformations of the polymers are then examined in various scenarios in a step-wise procedure, described below.

Polymers without side-chains are investigated in the gas phase. MD and/or MC methods are used to sample the conformations. The former is useful for global motions of the polymer. The latter, with biasing techniques (see Siepmann, J. K.; Martin, M. G.; and Vlugt, T. J. H., all of which are cited and incorporated by reference above), provides efficient sampling for polymers with multiple local minimum conformations that are separated by relatively large barriers.

The potential polymer candidates are then examined for positions to attach pendant groups that will impart amphiphilic character to the secondary structure.

The potential polymer candidates are further examined for positions to attach side chains and for which side chains to attach in order to help restrict rotation around the backbone bonds to enhance the amphiphilic character of the secondary structure.

Polymers with suitable backbone conformations and with side-chains at optimal positions selected from gas-phase studies are further evaluated in a model interfacial system, such as n-hexane/water. This model is preferable because it is relatively simple and computationally inexpensive, while mimicking a lipid/water bilayer environment. Alkane/water interface systems have been used effectively to represent membrane/water systems in studies of ion channels (112-118). See:

Zhong, Q. F., et al., "Molecular Dynamics Simulation of a Synthetic Ion Channel," Biophys. J., 74, 3-10 (1998);

Zhong, Q. F., et al., "The M2 Channel of Influenza A Virus: A Molecular Dynamics Study," FEBS Lett, 434 (1998);

Zhong, Q. F., et al., "Two Possible Conducting States of the Influenza A Virus M2 Ion Channel," FEBS Lett, 473 195-8 (2000);

Moore, P. B., et al., "Simulation of the HIV-1 Vpu Transmembrane Domain as a Pentameric Bundle," FEBS Lett., 431, 143-148 (1998);

Chipot, C., and Pohorille, A., "Structure and Dynamics of Small Peptides at Aqueous Interfaces: A Multi-Nanosecond Molecular Dynamics Study," Theo. J. Mol. Struct., 398, 529-535 (1997);

Chipot, C., et al., "Early Events in the Folding of an Amphiphathic Peptide: A Multinanosecond Molecular Dynamics Study," Proteins: Structure, Function and Genetics, 36, 383-399 (1999); and Pohorille, A., et al., "Interactions of Anesthetics with the Membrane-Water Interface," Chem. Phys., 204, 337-345 (1996); all of which are incorporated herein by reference in their entireties.

Alkane/water interface systems are utilized here to investigate conformation and partitioning behavior of the target polymers.

To reiterate, DFT calculations are performed on small model compounds, which then determine the torsional potentials for e.g. amide-aryl linkages and ether side chains. In an example, the barrier heights of the amide linkage for such compounds are generally higher than those of the amide linkage in peptides, reflecting the rigidification effects imposed by the neighboring benzene rings (conjugation) and the ether side chain (H-bonding). Since conventional force fields are developed for bio-molecules, they are generally not able to properly account for these effects. Thus, they could not correctly describe the rigidity of the polymer backbones and, correspondingly, could not be expected to correctly predict their conformations. This shows the importance of using modem high quality ab initio DFT methods to develop the torsional potentials. See also, Tew, Gregory N., et al., "De Novo Design of Biomimetic Antimicrobial Polymers," PNAS, vol. 99, no. 8, 5110-5114 (Apr. 16, 2002), incorporated herein by reference in its entirety.

The present invention is now described in view of example process flowcharts. The present invention is not, however, limited to the example flowcharts described herein. Based on the description herein, one skilled in the relevant art(s) will understand that the invention can be implemented with other process flowcharts as well. Such other process flowcharts fall within the spirit and scope of the present invention.

FIG. 1 illustrates an example process flowchart 100 for predicting conformation properties of polymer backbones. The process begins at Step 102, which includes identifying a target polymer backbone or portion thereof.

Step 104 includes identifying small model compounds that have structural connectivities that are similar to structural connectivities of the target polymer backbone or portion thereof, whereby the combination of the small model compounds serve as a model of the target polymer or portion thereof.

Figure 2:
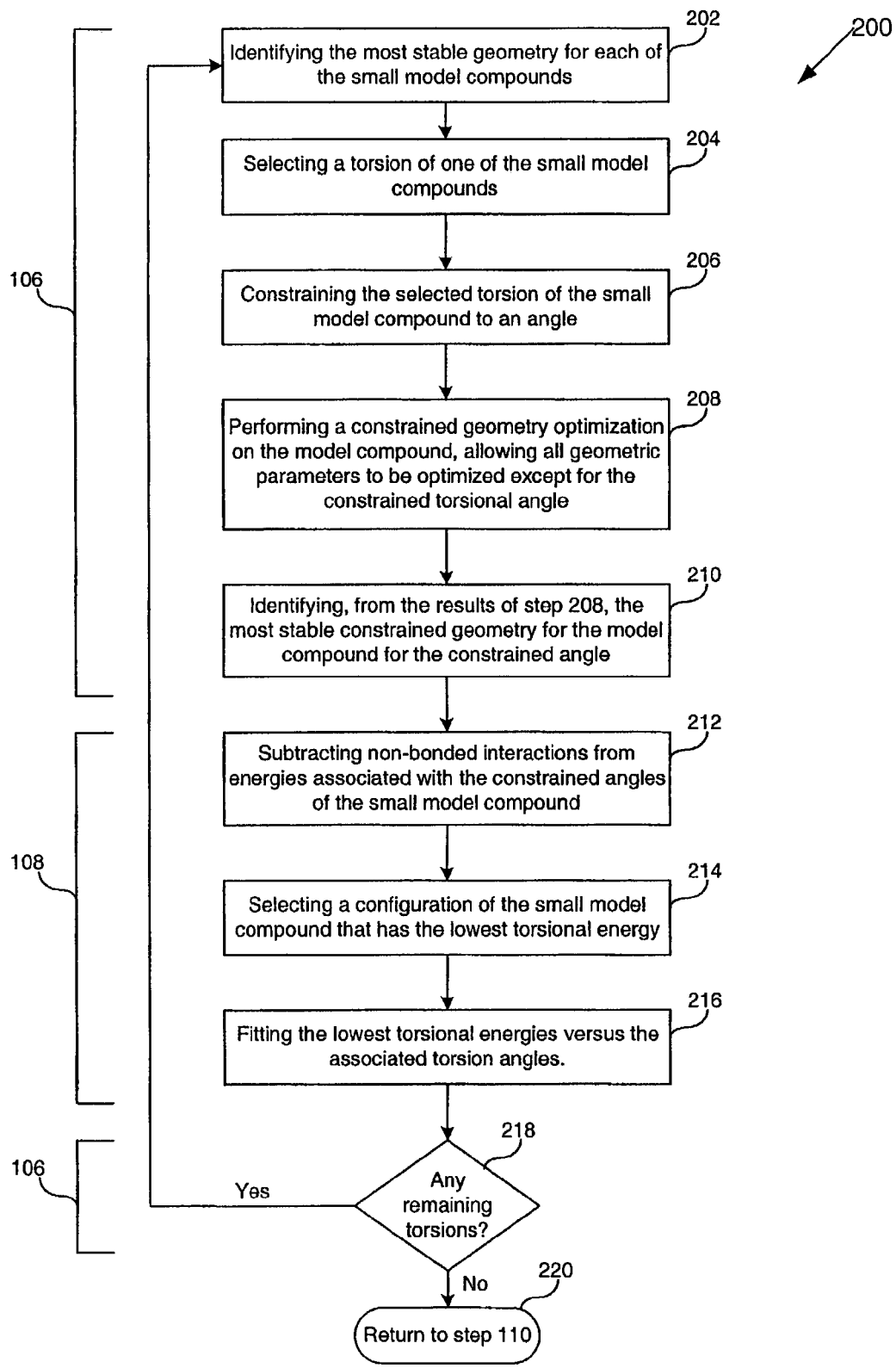
FIG. 2 is a process flowchart that illustrates an example method for obtaining new torsional parameters from the DFT torsional potentials, in accordance with the present invention.

Step 106 includes calculating gradient-corrected density functional theory ("DFT") torsional potentials for the small model compounds. Step 106 preferably includes selecting small model compounds that have torsional patterns that are similar to torsional patterns of the target polymer backbone. Step 106 preferably includes calculating energies at unconstrained and constrained geometries of the selected small model compounds. More particularly, Step 106 preferably includes calculating the energies at the unconstrained and constrained geometries using a parallelized plane-wave Car-Parrinello CPMD computer program. Preferably, the geometries are pre-optimized with simulated annealing in Step 106. Where full geometry optimization is performed on each of the small model compounds, using DFT, Step 106 can be implemented as illustrated in FIG. 2, which is described below.

Step 108 includes obtaining new torsional parameters from the DFT torsional potentials.

Step 110 includes combining the new torsional parameters with other terms to form a modified (or new) force field for the target polymer backbone or portion thereof.

Step 112 includes performing molecular dynamics and configurational-biased Monte Carlo ("MD/MC") simulations using the modified force field, whereby results of the MD/MC simulations serve as predicted conformation properties of the target polymer backbone.

Step 114 includes outputting the predicted conformation properties of the target polymer backbone.

Step 116 includes comparing results from the MD/MC simulations, using the modified force field against laboratory results for the small model compounds.

In Step 118, Steps 102-116 are optionally repeated for one or more additional target polymer backbones or portions thereof. In Step 120, the predicted conformation properties for the multiple target polymer backbones are used to select one or more of the multiple target polymer backbones as candidate polymer backbones, such as candidate amphiphilic polymer backbones, for synthesis.

FIG. 2 illustrates an example process flowchart 200 for implementing portions of the flowchart 100 when full geometry optimization is performed on each of the small model compounds in Step 106. The process begins at Step 202, which includes identifying, from the results of the full geometry DFT optimization, the most stable geometry for each of the small model compounds.

Step 204 includes selecting a torsion of one of the small model compounds.

Step 206 includes constraining the selected torsion of the small model compound to an angle.

Step 208 includes performing a constrained geometry optimization on the model compound, allowing all geometric parameters to be optimized except for the constrained torsional angle.

Step 210 includes identifying, from the results of Step 208, the most stable constrained geometry for the model compound for the constrained angle. Step 210 preferably includes calculating a single-point energy at the selected geometry.

In Step 212, if there are any remaining angles of the small model compound, Steps 206 through 210 are repeated. Otherwise, processing proceeds to Step 214.

Step 214 includes subtracting non-bonded interactions from energies associated with the constrained angles of the small model compound, whereby the result is an energy profile for the selected torsion of the small model compound.

Step 216 includes selecting a configuration or conformation of the small model compound that has the lowest torsional energy.

Step 218 includes fitting the lowest torsional energies of Step 216 versus the associated torsion angles for the selected configuration of the small model compound to a cosine series whose coefficients serve as force field parameters for the associated torsion in the modified force field for the polymer.

In Step 220, if there are any remaining torsions of the small model compounds, Steps 204 through 218 are repeated. Otherwise, processing proceeds to Step 110 in FIG. 1.

The DFT optimized geometries of Steps 108 and/or 202 for the target polymer or portion thereof are preferably used to determine one or more of the following:

structure of oligomers, monomeric units, or portions of a target molecules;

relative stabilities of particular conformations; and/or partial atomic charges and multipole moments that potentially have a bearing on the functioning of the target polymer.

Step 110 preferably includes combining the fitted torsional energies with bond stretching, bending, one-four, van der Waals, and electrostatic potentials obtained from CHARMM and TraPPE force fields, whereby the results serve as the modified force field for the target polymer.

The present invention can be implemented in one or more computer systems capable of carrying out the functionality described herein. For example, and without limitation, the process flowcharts 100 and/or 200, or portions thereof, can be implemented in a computer system.

Figure 3:
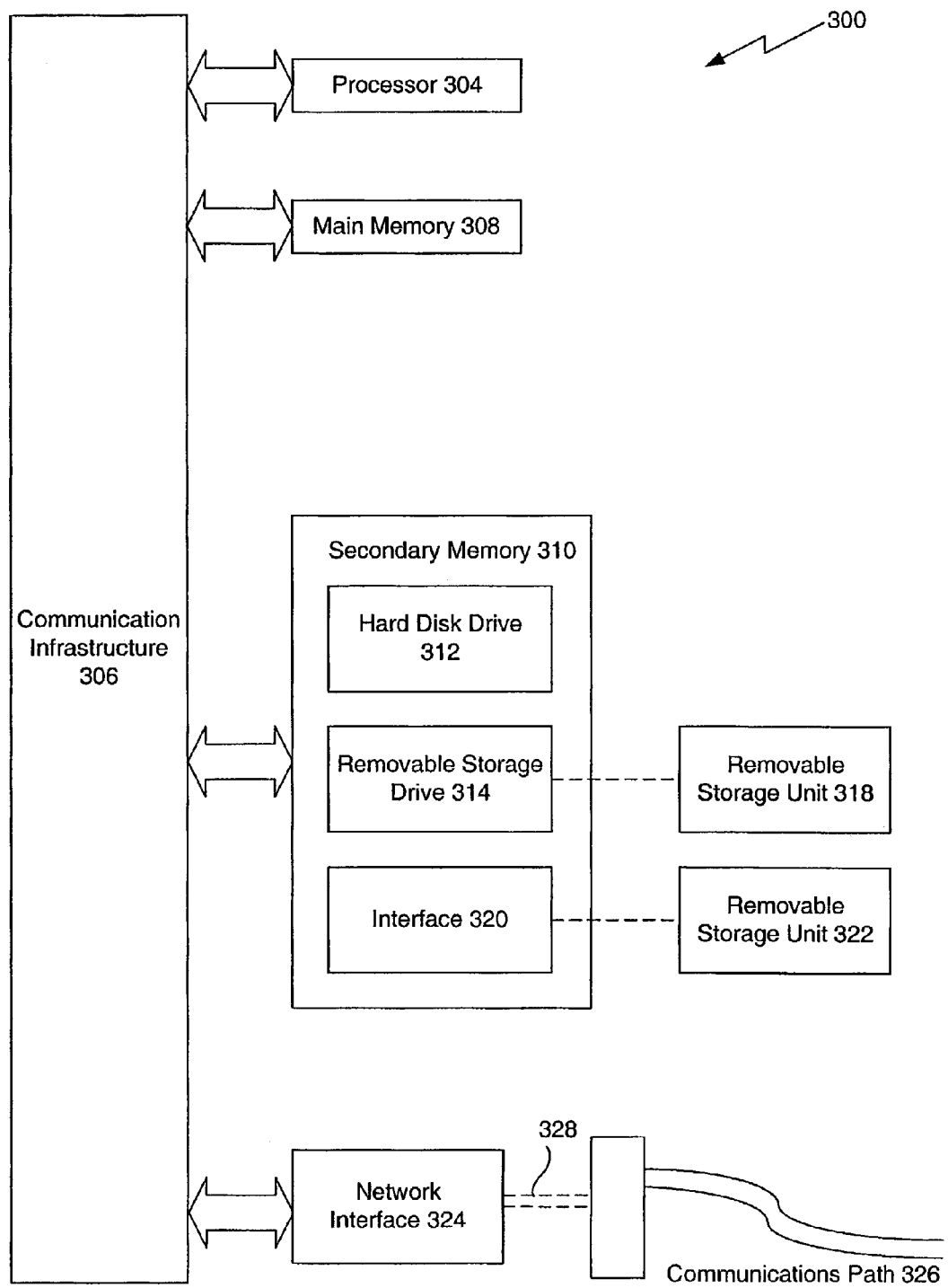
FIG. 3 is a block diagram of an example computer system on which the present invention can be implemented.

FIG. 3 illustrates an example computer system 300. Various software embodiments are described in terms of this example computer system 300. After reading this description, it will be apparent to a person skilled in the relevant art(s) how to implement the invention using other computer systems and/or computer architectures.

The example computer system 300 includes one or more processors 304. Processor 304 is connected to a communication infrastructure 306.

Computer system 300 also includes a main memory 308, preferably random access memory (RAM).

Computer system 300 can also include a secondary memory 310, which can include, for example, a hard disk drive 312 and/or a removable storage drive 314, which can be a floppy disk drive, a magnetic tape drive, an optical disk drive, etc. Removable storage drive 314 reads from and/or writes to a removable storage unit 318 in a well-known manner. Removable storage unit 318, represents a floppy disk, magnetic tape, optical disk, etc. which is read by and written to by removable storage drive 314. Removable storage unit 318 includes a computer usable storage medium having stored therein computer software and/or data.

In alternative embodiments, secondary memory 310 can include other devices that allow computer programs or other instructions to be loaded into computer system 300. Such devices can include, for example, a removable storage unit 322 and an interface 320. Examples of such can include a program cartridge and cartridge interface (such as that found in video game devices), a removable memory chip (such as an EPROM, or PROM) and associated socket, and other removable storage units 322 and interfaces 320 that allow software and data to be transferred from the removable storage unit 322 to computer system 300.

Computer system 300 can also include a communications interface 324, which allows software and data to be transferred between computer system 300 and external devices. Examples of communications interface 324 include, but are not limited to, a modem, a network interface (such as an Ethernet card), a communications port, a PCMCIA slot and card, etc. Software and data transferred via communications interface 324 are in the form of signals 328, which can be electronic, electromagnetic, optical or other signals capable of being received by communications interface 324. These signals 328 are provided to communications interface 324 via a signal path 326. Signal path 326 carries signals 328 and can be implemented using wire or cable, fiber optics, a phone line, a cellular phone link, an RF link and other communications channels.

In this document, the terms "computer program medium" and "computer usable medium" are used to generally refer to media such as removable storage unit 318, a hard disk installed in hard disk drive 312, and signals 328. These computer program products are means for providing software to computer system 300.

Computer programs (also called computer control logic) are stored in main memory 308 and/or secondary memory 310. Computer programs can also be received via communications interface 324. Such computer programs, when executed, enable the computer system 300 to perform the features of the present invention as discussed herein. In particular, the computer programs, when executed, enable the processor(s) 304 to perform the features of the present invention. Accordingly, such computer programs represent controllers of the computer system 300.

In an embodiment where the invention is implemented using software, the software can be stored in a computer program product and loaded into computer system 300 using removable storage drive 314, hard disk drive 312 or communications interface 324. The control logic (software), when executed by the processor(s) 304, causes the processor(s) 304 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

III. Conclusion

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like and combinations thereof.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for predicting conformations of polymer backbones, comprising:
    (1) identifying a target polymer backbone or portion thereof;
    (2) identifying small model compounds that have structural connectivities that are similar to structural connectivities of the target polymer backbone or portion thereof, whereby the combination of the small model compounds serve as a model of the target polymer or portion thereof;
    (3) computing gradient-corrected density functional theory ("DFT") torsional potentials for the small model compounds;
    (4) obtaining torsional parameters from the DFT torsional potentials;
    (5) combining the torsional parameters with other terms to form a force field for the target polymer backbone or portion thereof;
    (6) performing molecular dynamics and configurational-biased Monte Carlo ("MD/MC") simulations using the force field, whereby results of the MD/MC simulations serve as predicted conformations of the target polymer backbone;
    (7) outputting the predicted conformations of the target polymer backbone to a computer's memory;
    (8) verifying the accuracy of the force field against laboratory results for the small model compounds;
    (9) repeating steps (1) through (8) for one or more additional target polymer backbones or portions thereof;
    (10) using the predicted conformation for the target polymer backbones to select one or more of the target polymer backbones as candidate amphiphilic polymer backbones for synthesis; and
    (11) outputting the one or more target polymer backbones from step (10) to a display or in a user-readable format, wherein each of steps (1)-(11) is performed on a suitably programmed computer.

2. The method according to claim 1, wherein step (2) comprises selecting small model compounds that have torsional patterns that are similar to torsional patterns of the target polymer backbone.

3. The method according to claim 2, wherein step (3) comprises calculating energies at unconstrained and constrained geometries of the selected small model compounds.

4. The method according to claim 3, wherein step (3) further comprises calculating the energies at the unconstrained and constrained geometries using a parallelized plane-wave Car-Parrinello CPMD computer program.

5. The method according to claim 4, wherein step (3) further comprises using simulated annealing to pre-optimize the geometries, wherein said simulated annealing is performed on a suitably programmed computer.

6. The method according to claim 5, wherein step (3) further comprises:
    (a) performing a full geometry optimization on each of the small model compounds with DFT, wherein each said geometry optimization is performed on a suitably programmed computer.

7. The method according to claim 6, wherein step (3) further comprises:
    (a) identifying the most stable geometry for each of the small model compounds;
    (b) selecting a torsion of one of the small model compounds;

(c) constraining the selected torsion of the small model compound to an angle;

(d) performing a constrained geometry optimization on the model compound, allowing all geometric parameters to be optimized except for the constrained torsional angle;

(e) identifying, from the results of step (3)(d), the most stable constrained geometry for the model compound for the constrained angle;

(f) repeating steps (3)(c) through (3)(e) for additional angles of the small model compound;

(g) subtracting non-bonded interactions from energies associated with the constrained angles of the small model compound, whereby the result is an energy profile for the selected torsion of the small model compound;

(h) selecting a configuration or conformation of the small model compound that has the lowest torsional energy;

(i) fitting the lowest torsional energies of step (3)(h) versus the associated torsion angles for the selected configuration of the small model compound to a cosine series whose coefficients serve as force field parameters for the associated torsion in the modified force field for the polymer; and (j) repeating steps (3)(b) through (3)(i) for remaining torsions of the small model compounds, wherein each of steps (a)-(j) is performed on a suitably programmed computer.

8. The method according to claim 7, wherein step (3)(e) comprises calculating a single-point energy at a greater level of accuracy than the level of accuracy of the constrained geometry optimization.

9. The method according to claim 1, wherein step (5) further comprises combining the fitted torsional energies with bond stretching, bending, one-four, van der Waals, and electrostatic potentials obtained from CHARMM and TraPPE force fields, whereby the results serve as the modified force field for the target polymer, wherein said combining the fitted torsional energies is performed on a suitably programmed computer.

10. A computer program product comprising a removable storage unit or a hard disk installed in a hard disk drive having computer program logic stored therein, said computer program logic enabling a computer system to predict conformations of polymer backbones, said computer program logic comprising:

a first function that causes the computer system to identify a target polymer backbone or portion thereof;

a second function that causes the computer system to identify small model compounds that have structural connectivities that are similar to structural connectivities of the target polymer backbone or portion thereof, whereby the combination of the small model compounds serve as a model of the target polymer or portion thereof;

a third function that causes the computer system to calculate gradient-corrected density functional theory ("DFT") torsional potentials for the small model compounds;

a fourth function that causes the computer system to obtain torsional parameters from the DFT torsional potentials;

a fifth function that causes the computer system to combine the torsional parameters with other terms to form a force field for the target polymer backbone or portion thereof;

a sixth function that causes the computer system to perform molecular dynamics and configurational-biased Monte Carlo ("MD/MC") simulations using the force field, whereby results of the MD/MC simulations serve as predicted conformations of the target polymer backbone;

a seventh function that causes the computer system to output the predicted conformations of the target polymer backbone;

an eighth function that causes the computer system to verify the accuracy of the modified force field against laboratory results for the small model compounds;

a ninth function that causes the computer system to use the predicted conformations for the target polymer backbones to select one or more of the target polymer backbones as candidate amphiphilic polymer backbones for synthesis; and a tenth function outputting the one or more target polymer backbones from the previous function of the computer system to a display or in a user-readable format.

11. An apparatus for predicting conformations of polymer backbones, comprising:

means for identifying one or more target polymer backbone or portion thereof;

means for identifying small model compounds that have structural connectivities that are similar to structural connectivities of the target polymer backbone or portion thereof, whereby the combination of the small model compounds serve as a model of the target polymer or portion thereof;

means for calculating gradient-corrected density functional theory ("DFT") torsional potentials for the small model compounds;

means for obtaining torsional parameters from the DFT torsional potentials;

means for combining the torsional parameters with other terms to form a force field for the target polymer backbone or portion thereof;

means for performing molecular dynamics and configurational-biased Monte Carlo ("MD/MC") simulations using the force field, whereby results of the MD/MC simulations serve as predicted conformations of the target polymer backbone;

means for outputting the predicted conformations of the target polymer backbone; and means for verifying the accuracy of the modified force field against laboratory results for the small model compounds;

means for using the predicted conformations for the target polymer backbones to select one or more of the target polymer backbones as candidate amphiphilic polymer backbones for synthesis; and means for outputting the one or more target polymer backbones to a display or in a user-readable format.

* * * * *

UNITED STATES PATENT AND TRADEMARK OFFICE
CERTIFICATE OF CORRECTION

PATENT NO. : 7,590,517 B2  
APPLICATION NO. : 10/446171  
DATED : September 15, 2009  
INVENTOR(S) : Doerksen et al.

Page 1 of 1

It is certified that error appears in the above-identified patent and that said Letters Patent is hereby corrected as shown below:

In the Specification

Column 1, Lines 18-19, "Part of the work performed during development of this invention utilized U.S. Government funds." should be replaced by "This invention was made with government support under DMR9632598 awarded by the National Science Foundation."

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*